US012714792B2

(12) United States Patent
Li et al.

(10) Patent No.: US 12,714,792 B2
(45) Date of Patent: Aug. 25, 2026

(54) MULTISTAGE GAS-ACTUATED DRUG SUPPLY DEVICE AND METHOD THEREOF

(71) Applicant: MicroMED Co., Ltd., Taipei (TW)

(72) Inventors: Po-Ying Li, Taipei (TW); Kuang-Hsiang Cheng, Taipei (TW)

(73) Assignee: MicroMED Co., Ltd., Taipei (TW)

( * ) Notice: Subject to any disclaimer, the term of this patent is extended or adjusted under 35 U.S.C. 154(b) by 1057 days.

(21) Appl. No.: 17/517,000

(22) Filed: Nov. 2, 2021

(65) Prior Publication Data

US 2022/0152306 A1 May 19, 2022

Related U.S. Application Data

(60) Provisional application No. 63/115,223, filed on Nov. 18, 2020.

(51) Int. Cl.

*A61M 5/20* (2006.01)
*A61M 5/145* (2006.01)
*A61M 5/142* (2006.01)
*A61M 5/315* (2006.01)

(52) U.S. Cl.

CPC ........ *A61M 5/2046* (2013.01); *A61M 5/1452* (2013.01); *A61M 2005/14204* (2013.01); *A61M 5/31513* (2013.01)

(58) Field of Classification Search

CPC ...... A61M 5/2046; A61M 2005/14204; A61M 5/1452; A61M 3/0237; A61M 5/155; A61M 5/31511; A61M 5/315; A61M 5/142; A61M 5/31583; A61M 5/2429; A61M 5/31513; F15B 15/16

See application file for complete search history.

(56) References Cited

U.S. PATENT DOCUMENTS

| | | | | |
|---|---|---|---|---|
| 2,933,070 A * | 4/1960 | Trumper | F15B 15/16 | 91/169 |
| 3,128,674 A * | 4/1964 | Ganchar | F15B 15/16 | 91/169 |
| 3,136,221 A * | 6/1964 | Walker | F15B 15/16 | 91/401 |
| 3,253,592 A * | 5/1966 | Von Pechmann | A61M 5/178 | D24/114 |

(Continued)

FOREIGN PATENT DOCUMENTS

| | | | |
|---|---|---|---|
| EP | 2923713 A1 * | 9/2015 | A61M 1/0009 |
| GB | 2410782 A * | 8/2005 | B60R 21/38 |

*Primary Examiner* — Nilay J Shah

(74) *Attorney, Agent, or Firm* — Birch, Stewart, Kolasch & Birch, LLP

(57) ABSTRACT

A multistage gas-actuated drug supply device is connected to a drug injection container, the features include a gas supply unit, providing a gas; a plunger unit, composed of a plurality of hollow tubes, one end is connected to the gas supply unit, the hollow tubes can be stretched by the gas; a plunger top, connected to the other end of the plunger unit, pushing a medicament as the hollow tubes stretch; a gas chamber, penetrating the plunger unit, connected to the gas supply unit, holding the gas and stretching the hollow tubes as the gas increases, the gas chamber is further expanded; a limit part, located in the coupling end of the connected hollow tubes, limiting the collapsing length of the hollow tubes; and an airtight piece, located in the coupling end of the connected hollow tubes, sealing the gas chamber.

7 Claims, 15 Drawing Sheets

(56) References Cited

U.S. PATENT DOCUMENTS

| | | | | |
|---|---|---|---|---|
| 3,279,755 | A * | 10/1966 | Notenboom | F15B 15/1414<br>91/169 |
| 3,832,937 | A * | 9/1974 | Moore | F15B 15/16<br>91/446 |
| 4,936,193 | A * | 6/1990 | Stoll | F15B 15/16<br>92/52 |
| 5,341,724 | A * | 8/1994 | Vatel | F15B 15/16<br>91/1 |
| 9,568,028 | B2 * | 2/2017 | Nowak | F15B 15/16 |
| 2007/0066939 | A1 * | 3/2007 | Krulevitch | A61M 5/1452<br>604/152 |
| 2013/0304021 | A1 * | 11/2013 | Cabiri | A61M 5/31511<br>604/506 |

* cited by examiner

MULTISTAGE GAS-ACTUATED DRUG SUPPLY DEVICE AND METHOD THEREOF

CROSS-REFERENCE TO RELATED APPLICATIONS

This Non-provisional application claims priority under 35 U.S.C. § 119(a) on Patent Application No. [63/115,223] filed in American United Sates Nov. 18, 2020, the entire contents of which are hereby incorporated by reference.

FIELD OF THE INVENTION

The present invention relates generally to a multistage gas-actuated drug supply device, and more particularly to the actuated drug supply device and method for small volumes and preventing gas leakage.

BACKGROUND OF INVENTION

For the treatment of many chronic diseases, subcutaneous application of drugs or therapeutic agents shall be performed at continuous or specific time intervals with accurately controlled dosage of drugs. The subcutaneous injection is a useful route for delivering drugs into the body, the drugs are absorbed more slowly (compared with direct injection into blood vessels). At present, pen-type or patch-type injectors using primary containers (prefilled syringe or prefilled cartridge) such as pen injector, auto-injector and wearable injector have been developed to allow, the users to inject drugs into their bodies by themselves. However, these conventional injectors using a spring or a miniature motor can generate unstable driving force induced by the spring or motor and cause unexpected pains during the drug injection process.

Additionally, some treatments require injection volume greater than 1 ml, which exceeds the volume limit of the existing subcutaneous injection device, and the injection speed for these devices are either too fast (several seconds) or too slow (several hours or days). For example, the volumes of intravenous injection for conventional protein drugs usually exceed 30 mL (some even reaches 250 mL). Their injection time is usually from 30 minutes to several hours. Therefore, if portable/wearable subcutaneous injection devices can be used with reformulated and more concentrated protein drugs (with reduced volume from 30-250 mL to 1-20 mL), patients can then self inject drug at home which will save patient lots of time and greatly enhanced their live quality. However, due to the solubility limit for the protein drugs, the volume of these biological drugs is usually greater than 1 mL. This minimum volume limit when concentrating the protein types of drugs is mainly due to the precipitation nature of protein when reaching its solubility limit during the concentrating process. Therefore, many reformulated subcutaneous protein therapeutics are with volume much larger than 1 mL which may induce greater pain at the injection site of the patient. These are the reasoning why many of the existing pen injector or auto-injector products on the market are with injection volume less than 1 mL. In addition, many wearable pump products are driven by stepping motors (or similar mechanisms with rotating gears) with discrete (one pulse of drug injection with each gear step), not continuous mode of injection. Therefore, the associated delivery flow rate profile generated by the stepping motor is also in discrete mode (one droplet/pulse each time). For example, for commercial insulin pump products on the market, a typical dosage regimen for the pumps at 0.05 U/Hr is actually pushing a discrete drug droplet of 0.5 μL (0.05 U) each step and completely off for the rest of the hour. The maximum speed of the pump is at 600 deliveries per hour (30 U/Hr) which usually takes more than 3 hours to deliver 1 mL of the drug. This injection speed is slow and cannot meet the subcutaneous drug injection requirement of 5-10 minutes.

The existing electrochemical pumps usually utilize the electrochemically generated gases to directly act/apply force at the drug isolation component (e.g. diaphragm or movable barrier) to discharge the drug from the drug container. In this administration process, a drug contamination risk exists as the electrochemically generated high pressure leads to gas leakage through the drug isolation component (e.g. defects in diaphragm, wall of container or movable barrier).

Therefore, there is an urgent need to develop a drug supply device with small device footprint and reasonable gas production rate that can prevent the gas from contaminating the medicament.

SUMMARY OF THE INVENTION

The present invention is a multistage gas-actuated drug supply device, the device includes: a gas supply unit, providing a gas; a plunger unit, comprising a plurality of hollow tubes, one end is connected to the gas supply unit; a plunger top, connected to the other end of the plunger unit; a gas chamber, penetrating the plunger unit, connected to the gas supply unit; a limit part, the coupling end of the connected hollow tubes, the limit part limits the stretched length of the hollow tubes; an airtight piece, the coupling end of the connected hollow tubes, the airtight piece prevents the gas from leaking out of the gas chamber.

The gas supply unit of the present invention includes an electrochemical pump, the electrochemical pump can release the gas at a linear or nonlinear rate, or slowly release the gas to push the plunger unit; it is noteworthy that the present invention can administer drugs according to the requirements for the injection site or/and the delivery rate of different drugs, so that the injection receiver will not feel discomforted.

An embodiment of the present invention: a multistage gas-actuated drug supply method, the method includes: a gas supply unit, continuously supplying a gas increased at a linear or nonlinear rate in a period of time; a gas chamber covered in a plunger unit filled with the gas; as the pressure of the gas received by the gas chamber increases, the plurality of hollow tubes of the plunger unit stretch with the linear or nonlinear speed simultaneously; as the plunger unit stretches, the movable barrier of a drug injection container is pushed to push a medicament.

The present invention, an airtight piece, the coupling end of the connected hollow tubes, the airtight piece prevents the gas from leaking out of the gas chamber, effectively preventing the gas from contaminating the supplied medicament.

DETAILED DESCRIPTION OF THE INVENTION

Figure 1:
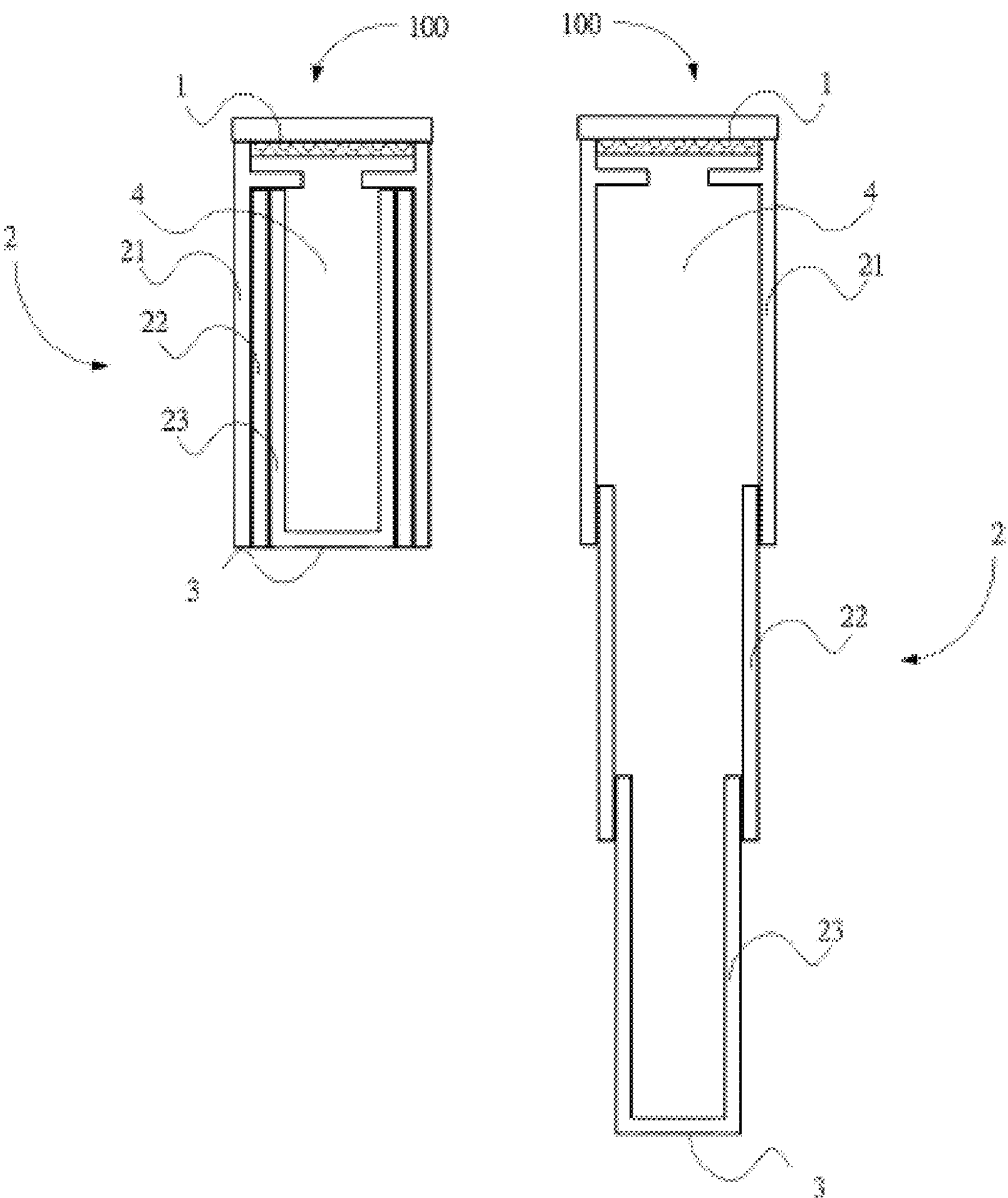
FIG. 1 Schematic diagram of multistage gas-actuated drug supply device
Figure 13:
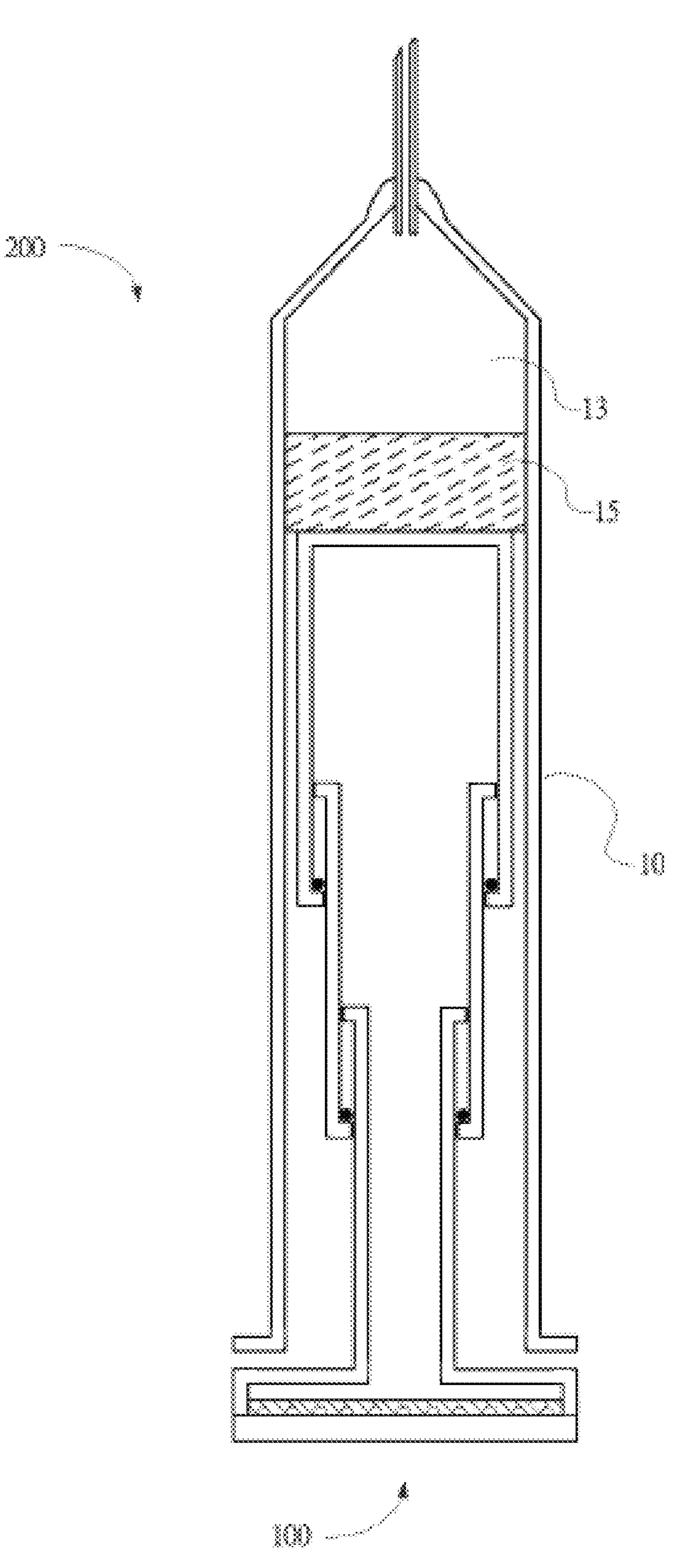
FIG. 13 Schematic diagram of injection needle of drug supply actuating device.

The present invention is a multistage gas-actuated drug supply device 100, as shown in [FIG. 1] and [FIG. 13], which can be used by connecting a drug injection container 10, the device includes:

- a gas supply unit 1, providing a gas;
- a plunger unit 2, comprising a plurality of hollow tubes, one end is connected to the gas supply unit 1, the hollow tubes can be stretched by the gas;
- a plunger top 3, connected to the other end of the plunger unit 2, pushing a movable barrier 15 as the hollow tubes stretch, and then a medicament 13 is pushed;
- a gas chamber 4, penetrating the plunger unit 2, connected to the gas supply unit 1, holding the gas and stretching the hollow tubes as the gas increases, and then the gas chamber 4 is expanded;
- the plunger unit 2 is not stretched and in the shortest state before the gas supply unit 1 is actuated; when the gas supply unit 1 supplies gas, the stretched length of the plunger unit 2 is shorter than the total length of the hollow tubes.

The gas supply unit 1 of the present invention includes an electrochemical pump, the electrochemical pump can release the gas at a linear or nonlinear rate, or slowly release the gas to push the plunger unit 2; it is noteworthy that the present invention can administer drugs according to the injection site or/and the delivery rate of different drugs, so that the injection receiver will not feel discomforted.

Figure 2:
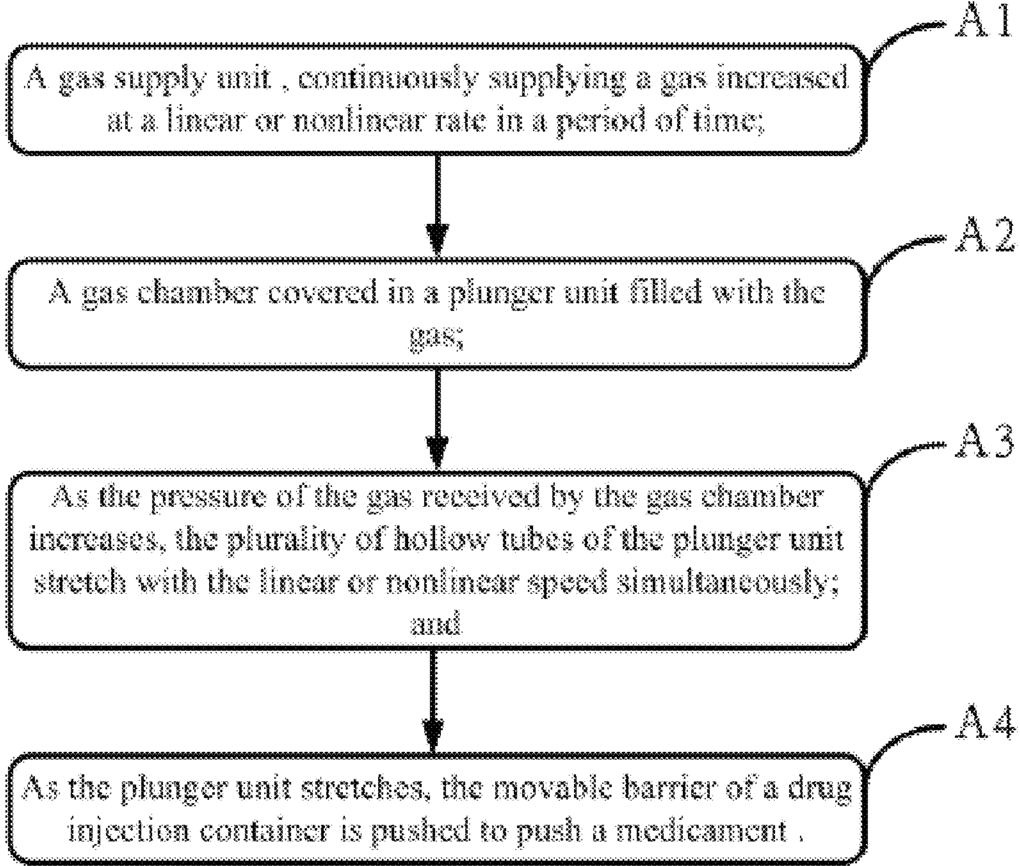
FIG. 2 Flow diagram of multistage gas-actuated drug supply method

An embodiment of the present invention, a multistage gas-actuated drug supply method is shown in [FIG. 2], the method includes:

- A1. A gas supply unit 1, continuously supplying a gas increased at a linear or nonlinear rate in a period of time;
- A2. A gas chamber 4 covered in a plunger unit 2 filled with the gas;
- A3. As the pressure of the gas received by the gas chamber 4 increases, the plurality of hollow tubes of the plunger unit 2 stretch with the linear or nonlinear speed simultaneously; and
- A4. As the plunger unit 2 stretches, the movable barrier 15 of a drug injection container is pushed to push a medicament 13.

Preferably, the movable barrier 15 includes a rubber stopper and a piston.

Figure 3:
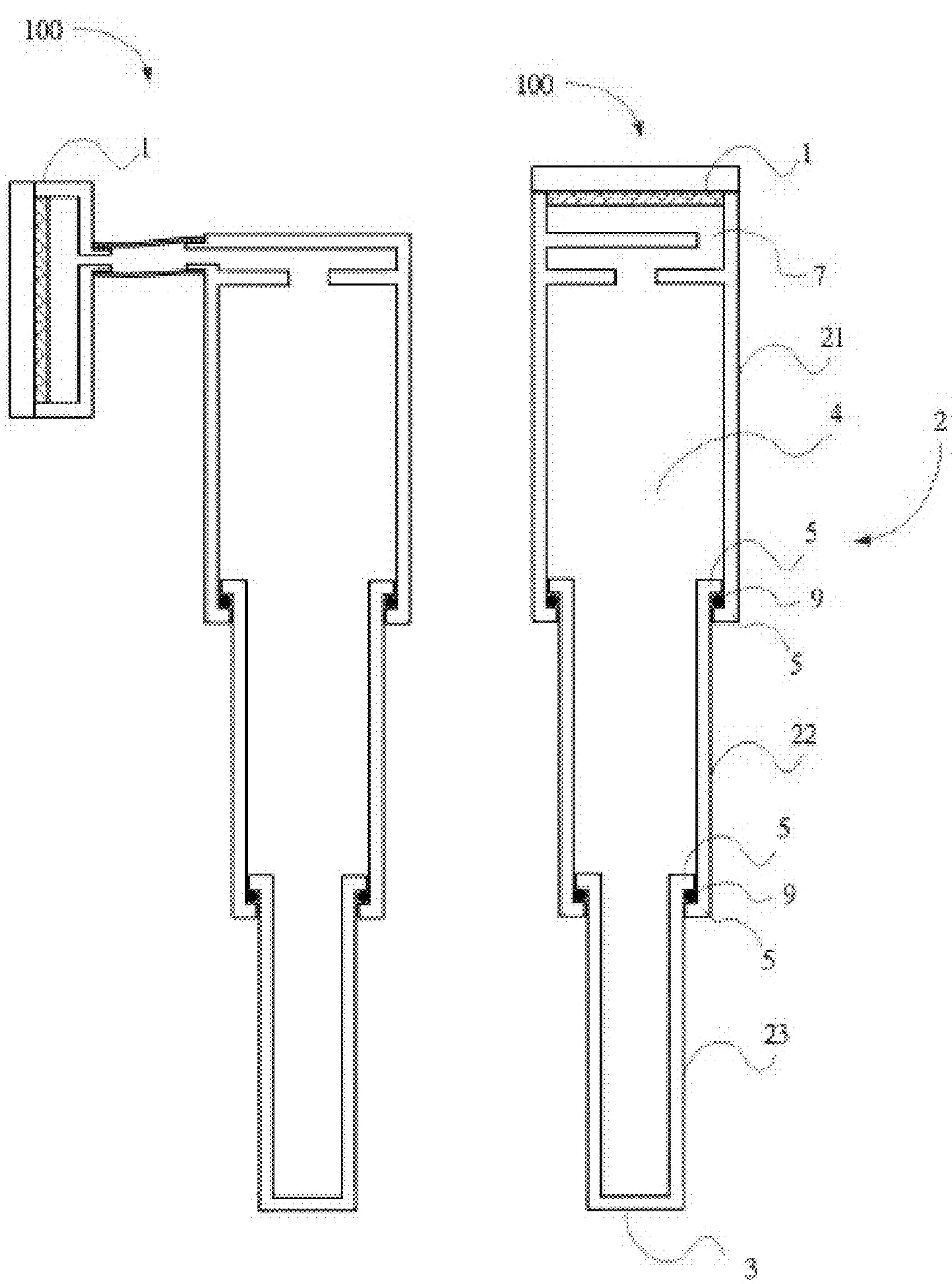
FIG. 3 Schematic diagram of buffer gas chamber and gas supply separation.

An embodiment of the present invention, a multistage gas-actuated drug supply device 100, as shown in [FIG. 3], the hollow tubes of the plunger unit 2, the coupling end of the connected hollow tubes has an airtight piece 9 and a limit part 5, the airtight piece 9 prevents the gas from leaking out of the gas chamber 4, effectively preventing the gas from contaminating the supplied medicament; the limit part 5 limits the stretched length of the hollow tubes.

An embodiment of the present invention, a multistage gas-actuated drug supply device 100, as shown in [FIG. 3], the gas supply unit 1 is connected to a buffer gas chamber 7 and to the plunger unit 2; the buffer gas chamber 7 prevents the gas generated by the gas supply unit from directly impacting the plunger unit 2, so that the plunger unit 2 can be stretched stably; the shape of the buffer gas chamber 7 shown in the figure is only an embodiment, the present invention is not limited to this shape.

An embodiment of the present invention, a multistage gas-actuated drug supply device 100, as shown in [FIG. 3], the gas supply unit 1 can be separate type and connected to the plunger unit 2 by a connecting tube.

An embodiment of the present invention, the plunger unit 2 comprises hollow tubes in descending order of tube diameter, the inside diameter of a No. N hollow tube is slightly larger than the outside diameter of a No. N+1 hollow tube, so that the No. N+1 hollow tube can slide inside the No. N hollow tube; N is the section number of the hollow tube 20.

An embodiment of the present invention, as shown in [FIG. 1], the plunger unit 2 comprises three sections of hollow tubes, including a first hollow tube 21 with one end connected to the gas supply unit 1 and the other end connected to a second hollow tube 22, the outside diameter of the second hollow tube 22 is slightly smaller than the inside diameter of the first hollow tube 21, so that the second hollow tube 22 can slide inside the first hollow tube 21; a third hollow tube 23 connected to the second hollow tube 22, the outside diameter of the third hollow tube 23 is slightly smaller than the inside diameter of the second hollow tube 22, so that the third hollow tube 23 can slide inside the second hollow tube 22, the other end of the third hollow tube 23 is connected to a plunger top 3.

An embodiment of the present invention, the plunger unit 2 comprises hollow tubes in ascending order of tube diameter, the outside diameter of a No. N hollow tube is slightly smaller than the inside diameter of a No. N+1 hollow tube, so that the No. N hollow tube can slide inside the No. N+1 hollow tube; N is the section number of the hollow tube 20.

Figure 4:
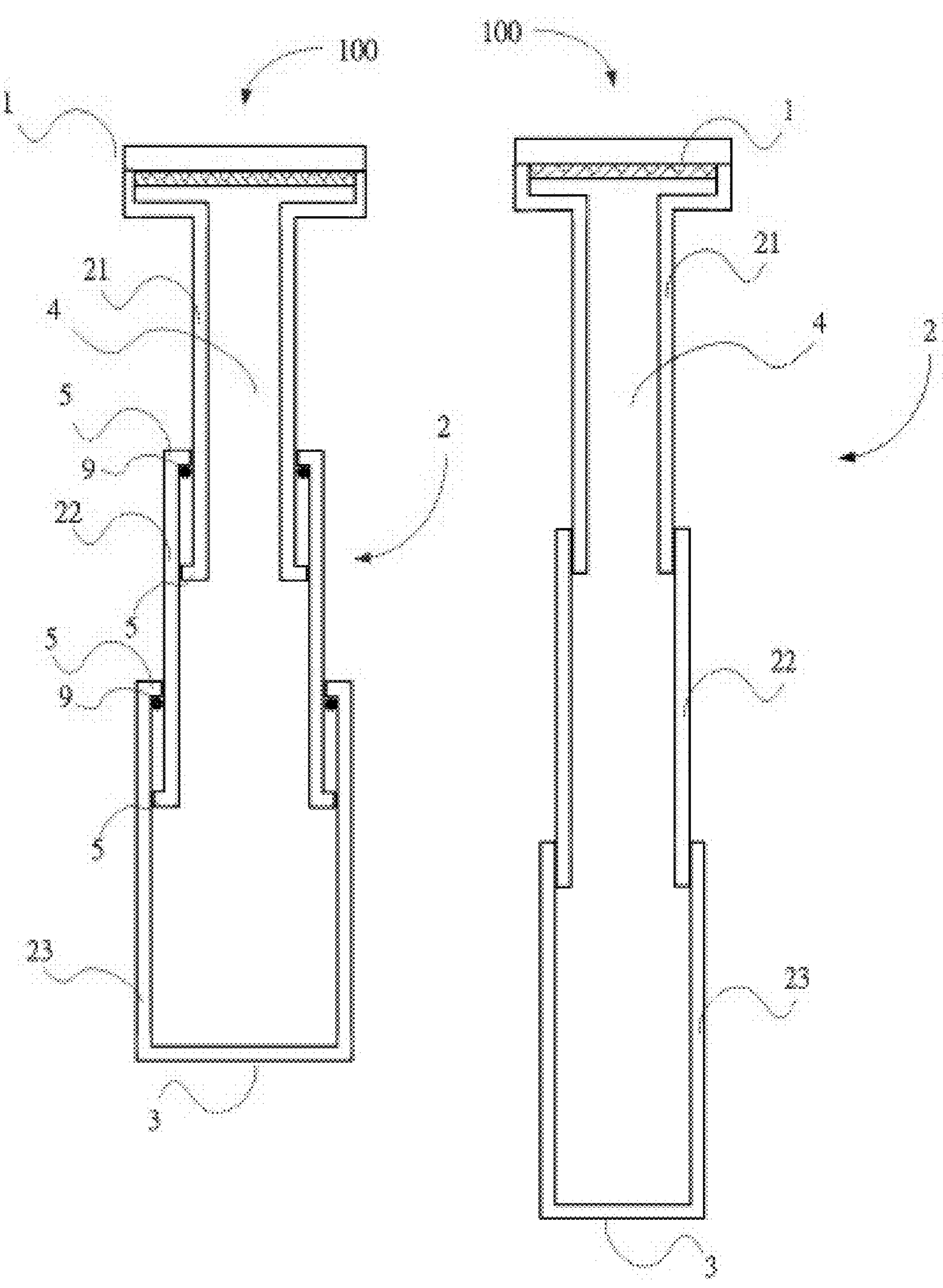
FIG. 4 Schematic diagram of plunger unit of small to large hollow tubes.

An embodiment of the present invention, as shown in [FIG. 4], the plunger unit 2 comprises three sections of hollow tubes, including a first hollow tube 21 with one end connected to the gas supply unit 1 and the other end connected to a second hollow tube 22, the outside diameter of the first hollow tube 21 is slightly smaller than the inside diameter of the second hollow tube 22, so that the first hollow tube 21 can slide inside the second hollow tube 22; a third hollow tube 23 connected to the second hollow tube 22, the outside diameter of the second hollow tube 22 is slightly smaller than the inside diameter of the third hollow tube 23, so that the second hollow tube 22 can slide inside the third hollow tube 23, the other end of the third hollow tube 23 is connected to a plunger top 3.

Figure 5:
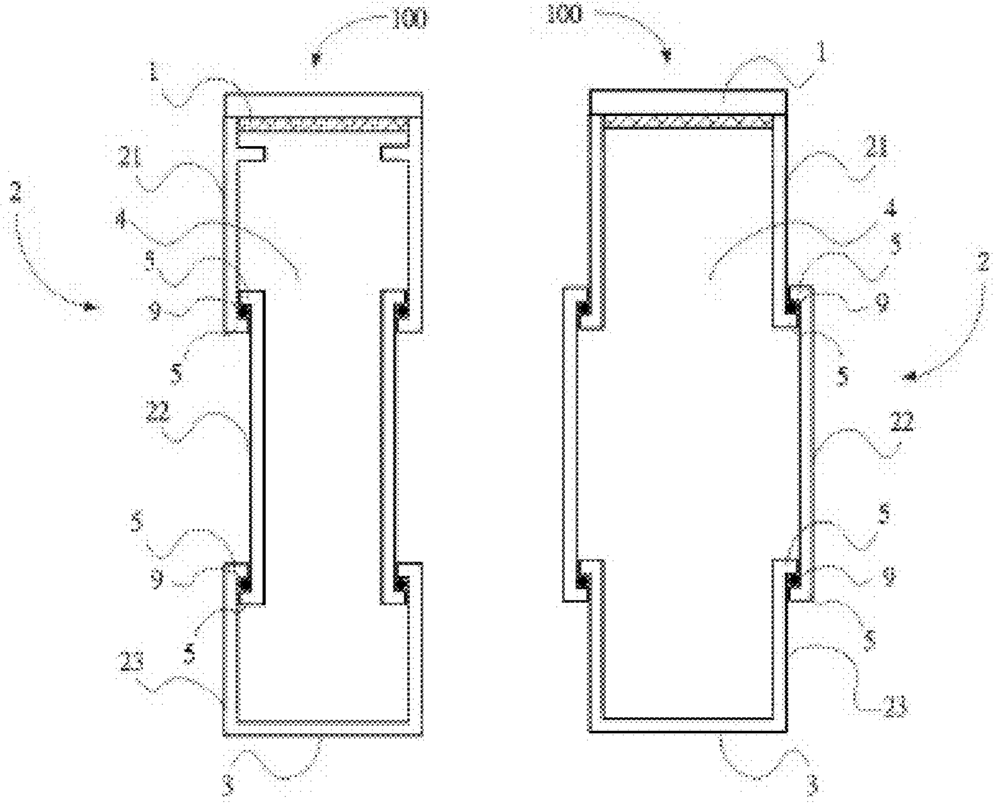
FIG. 5 Schematic diagram of plunger unit of different forms of hollow tubes.

An embodiment of the present invention, the plunger unit of different forms of hollow tubes is shown in the right figure of [FIG. 5], the plunger unit 2 comprises three sections of hollow tubes, including a first hollow tube 21 with one end connected to the gas supply unit 1 and the other end connected to a second hollow tube 22, the outside diameter of the first hollow tube 21 is slightly smaller than the inside diameter of the second hollow tube 22, so that the first hollow tube 21 can slide inside the second hollow tube 22; a third hollow tube 23 connected to the second hollow tube 22, the inside diameter of the second hollow tube 22 is slightly larger than the outside diameter of the third hollow tube 23, so that the third hollow tube 23 can slide inside the second hollow tube 22, the other end of the third hollow tube 23 is connected to a plunger top 3.

An embodiment of the present invention, the plunger unit of different forms of hollow tubes is shown in the left figure of [FIG. 5], the plunger unit 2 comprises three sections of hollow tubes, including a first hollow tube 21 with one end connected to the gas supply unit 1 and the other end connected to a second hollow tube 22, the inside diameter of the first hollow tube 21 is slightly larger than the outside diameter of the second hollow tube 22, so that the second hollow tube 22 can slide inside the first hollow tube 21; a third hollow tube 23 connected to the second hollow tube 22, the outside diameter of the second hollow tube 22 is slightly smaller than the inside diameter of the third hollow tube 23, so that the second hollow tube 22 can slide inside the third hollow tube 23, the other end of the third hollow tube 23 is connected to a plunger top 3.

Figure 6:
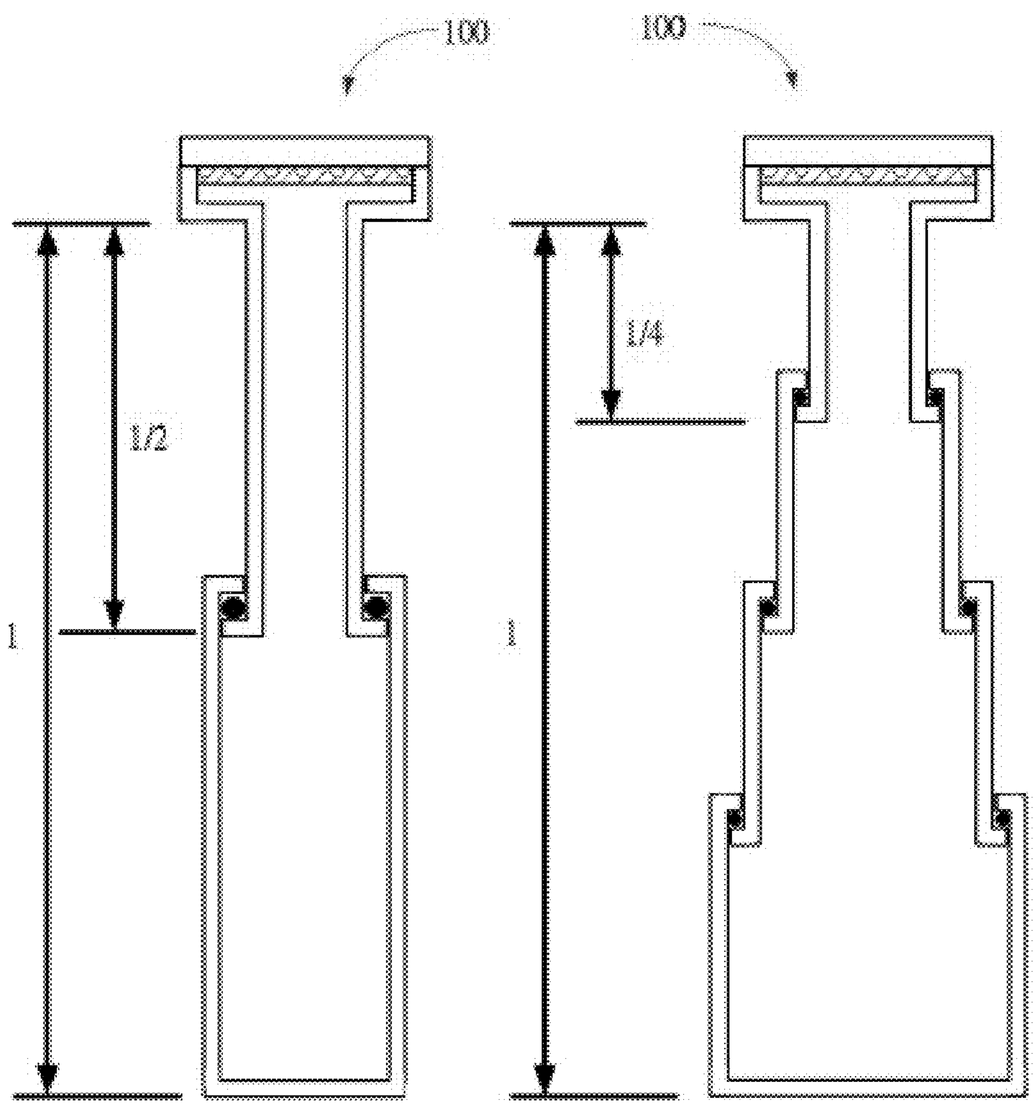
FIG. 6 Schematic diagram of plunger unit of multistage hollow tube.

An embodiment of the present invention, the plunger unit of multistage hollow tube is shown in [FIG. 6], the plunger unit 2 can be composed of a plurality of hollow tubes, including two-stage hollow tube (left figure) and four-stage hollow tube (right figure); the length of the two-stage hollow tube before it is stretched is ½ of total length, the length of the four-stage hollow tube before it is stretched is ¼ of total length, the present invention can effectively reduce the device size to save space.

Preferably, the multistage gas-actuated drug supply device 100, the length of the plunger unit 2 can be reduced to 1 mm before it is stretched.

Preferably, the contact area with the hollow tube varies with the shape and material of the airtight piece 9, and then the rate of stretch of the hollow tubes is influenced; the airtight piece 9 adheres to the hollow tubes to form a contact area, the contact area is inversely proportional to the rate of stretch of the hollow tube.

Figure 7:
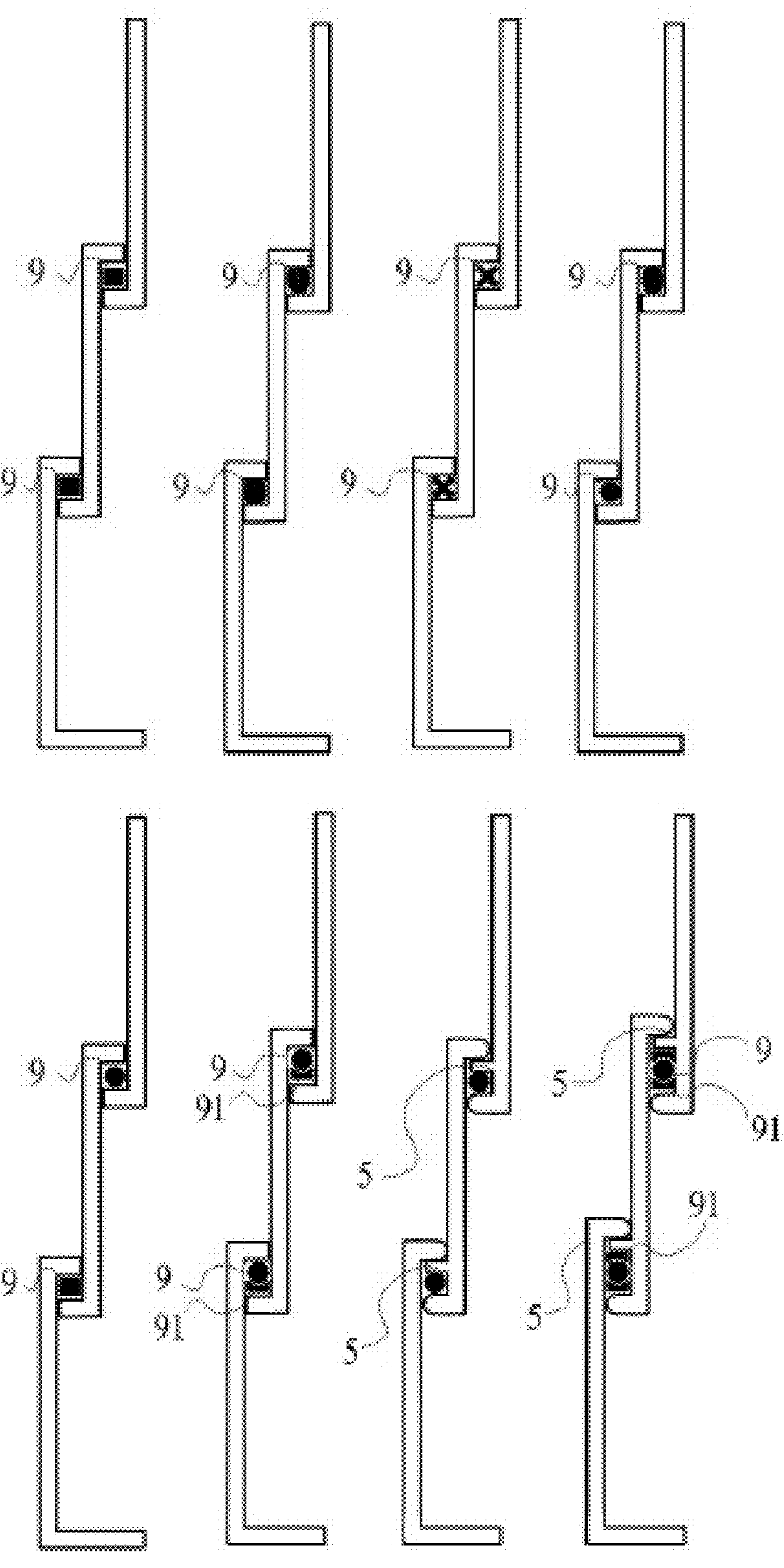
FIG. 7 Schematic diagram of design form with different airtight pieces and concave forms.

An embodiment of the present invention, a multistage gas-actuated drug supply device 100 is shown in [FIG. 7], the airtight piece 9 can be circular, quadrangular, elliptical, polygonal and X-shaped; each form has a different rate of stretch of the hollow tubes.

In the said embodiment, the airtight piece 9 can be used together, as shown in [FIG. 7], multiple patterns can be used together; the rate of stretch of the hollow tubes of each assorted form depends on the form of the airtight piece 9; it is noteworthy that the assorted design can work out the time-speed curve of medicament supply which is least likely to discomfort the medicament receiver according to different medicament properties or/and different subcutaneous tissue characteristics.

Preferably, as shown in [FIG. 7], the airtight piece 9 can be used with one or more than one backup ring 91, so as to improve the deformation when the airtight piece 9 stretches in the hollow tubes under high pressure.

Preferably, as shown in [FIG. 7], the limit part 5 is designed in concave form, the side edge height of concave form is lower than the height of the airtight piece 9, the positioning of the airtight piece 9 is enhanced to guarantee airtightness.

An embodiment of the present invention, as shown in [FIG. 8], the hollow tubes of the plunger unit can be directly designed as different caliber sizes or/and designed as different tube wall thicknesses, the relationship between the stressed area (A) and normal force (F) of pressure (P) of the gas released from the gas supply unit 1 is changed indirectly; expressed as follows $$\text{Pressure } (P)=\text{normal force } (F)/\text{stressed area } (A)\ [P=F/A]$$

Under the fixed pressure (P) provided by the gas supply unit 1, the stressed area (A) is proportional to the normal force (F) of rate of stretch, the larger the stressed area (A) is, the higher is the rate of stretch; furthermore, the sequence and rate of stretch of the hollow tubes can be changed and controlled by changing the ratio of the inside diameter to tube wall thickness of the hollow tubes, so as to implement variable and controllable drug supply rate curve.

Figure 8:
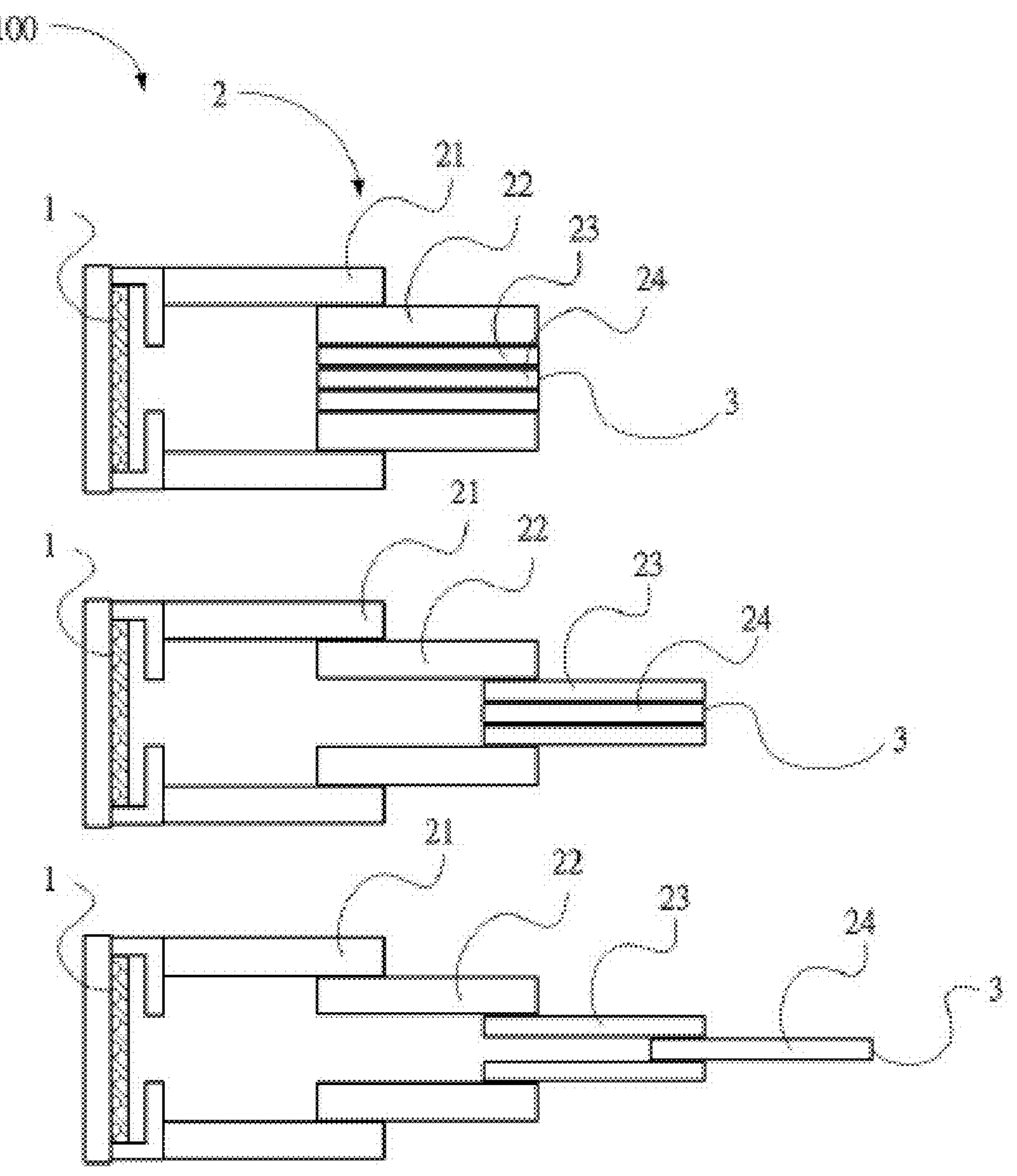
FIG. 8 Schematic diagram of variation in stressed area of plunger unit.
Figure 15:
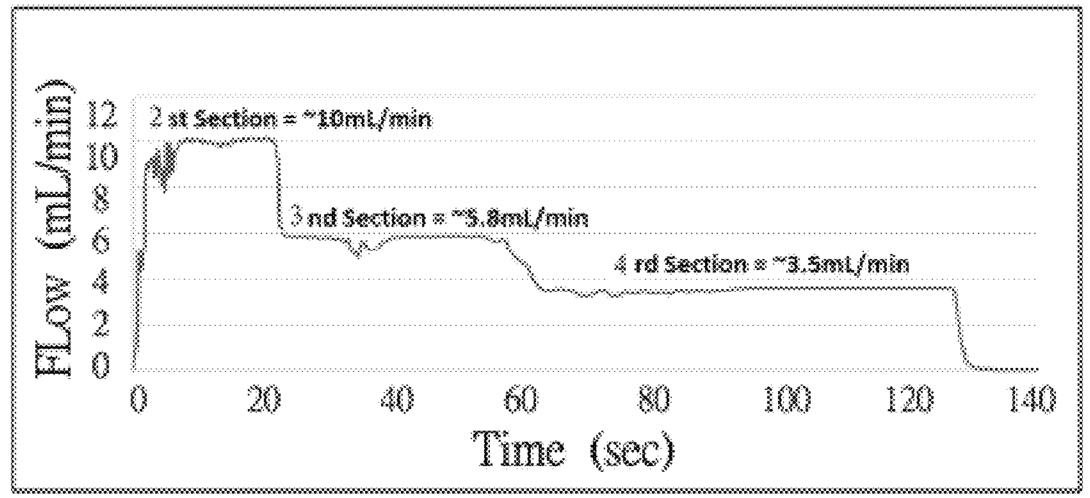
FIG. 15 Curve diagram of different drug supply speeds.

An embodiment of the present invention, a four-stage gas-actuated drug supply device is shown in [FIG. 8], the plunger unit 2 is assorted with the drug injection container 10 to implement different drug supply speed curves; the first hollow tube 21 is fixed to the gas supply unit 1, the gas supply unit 1 provides fixed pressure (P), in the first stage, the maximum normal force (F1) of stressed area (A1) is the highest before the plunger unit is stretched (A1=area of the plunger top 3+wall thickness of the second and third hollow tubes 22, 23×2), the flow is the highest 1st; in the second stage, the stressed area when the second hollow tube 22 has been stretched (A2=area of the plunger top 3+wall thickness of the third hollow tube 23×2), the flow takes second place 2nd; in the third stage, the stressed area when the third hollow tube 23 has been stretched (A3=area of the plunger top 3), the flow is the minimum 3rd; [FIG. 15] is the graph of relation between time and the medicament flow.

An embodiment of the present invention, the inner surface roughness of the hollow tubes of the plunger unit can be designed according to the actual sequence of stretch and rate of stretch; as the roughness of inner surface of the hollow tubes is inversely proportional to the rate of stretch of the hollow tubes (the higher the roughness is, the lower is the rate of stretch), the sequence and rate of stretch of the hollow tubes can be changed and controlled by changing the ratio of roughness of inner surface of the hollow tubes, so as to implement variable and controllable drug supply rate curve.

Figure 9:
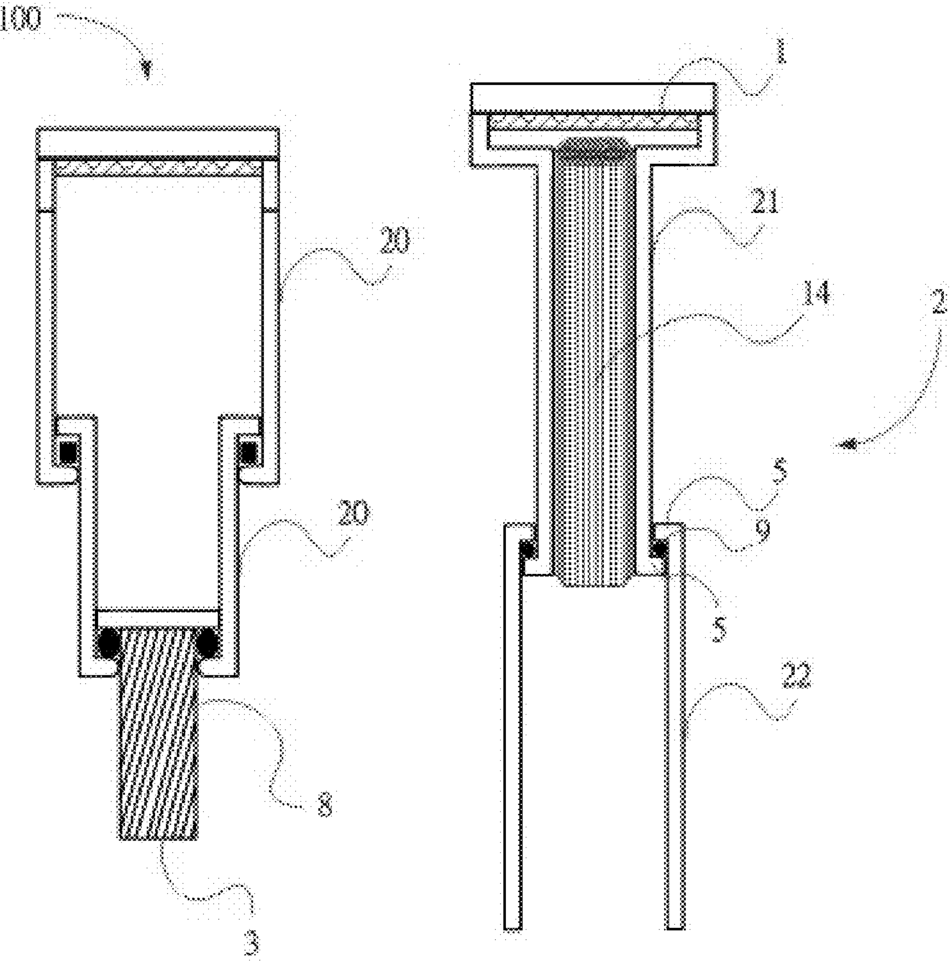
FIG. 9 Schematic diagram of cylinder component and capillary hollow tube.

An embodiment of the present invention, a multistage gas-actuated drug supply device 100 is shown in the left figure of [FIG. 9], the end section of the plunger unit 2 is a cylinder component 8, the cylinder component 8 is free of the gas chamber 4, the gas directly pushes one end of the cylinder component 8, the other end is the plunger top 3.

An embodiment of the present invention, a multistage gas-actuated drug supply device 100 is shown in the right figure of [FIG. 9], the first hollow tube 21 can be a capillary hollow tube 14 structure.

Figure 10:
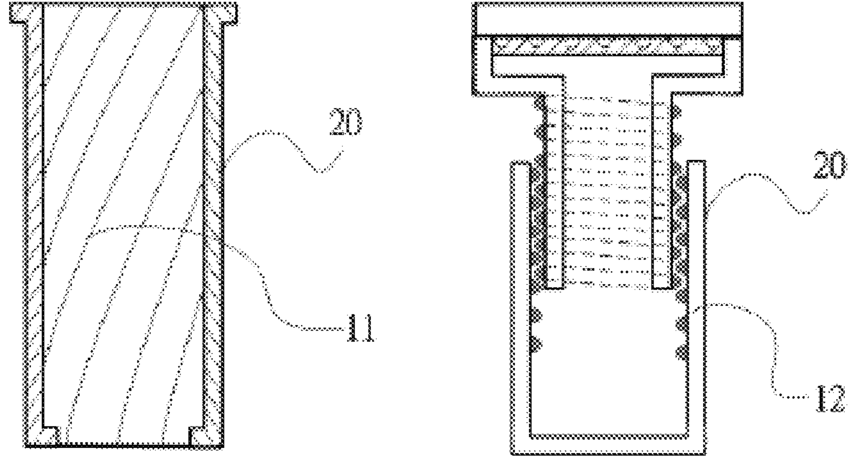
FIG. 10 Schematic diagram of major and minor helices.

An embodiment of the present invention, a multistage gas-actuated drug supply device 100, as shown in the sectional view of hollow tube in [FIG. 10], the inner wall of a hollow tube 20 of the plunger unit 2 is designed with a plurality of helices, so that the hollow tubes of the plunger unit 2 can be stretched helically; the helices include minor helix 11 and major helix 12.

Figure 11:
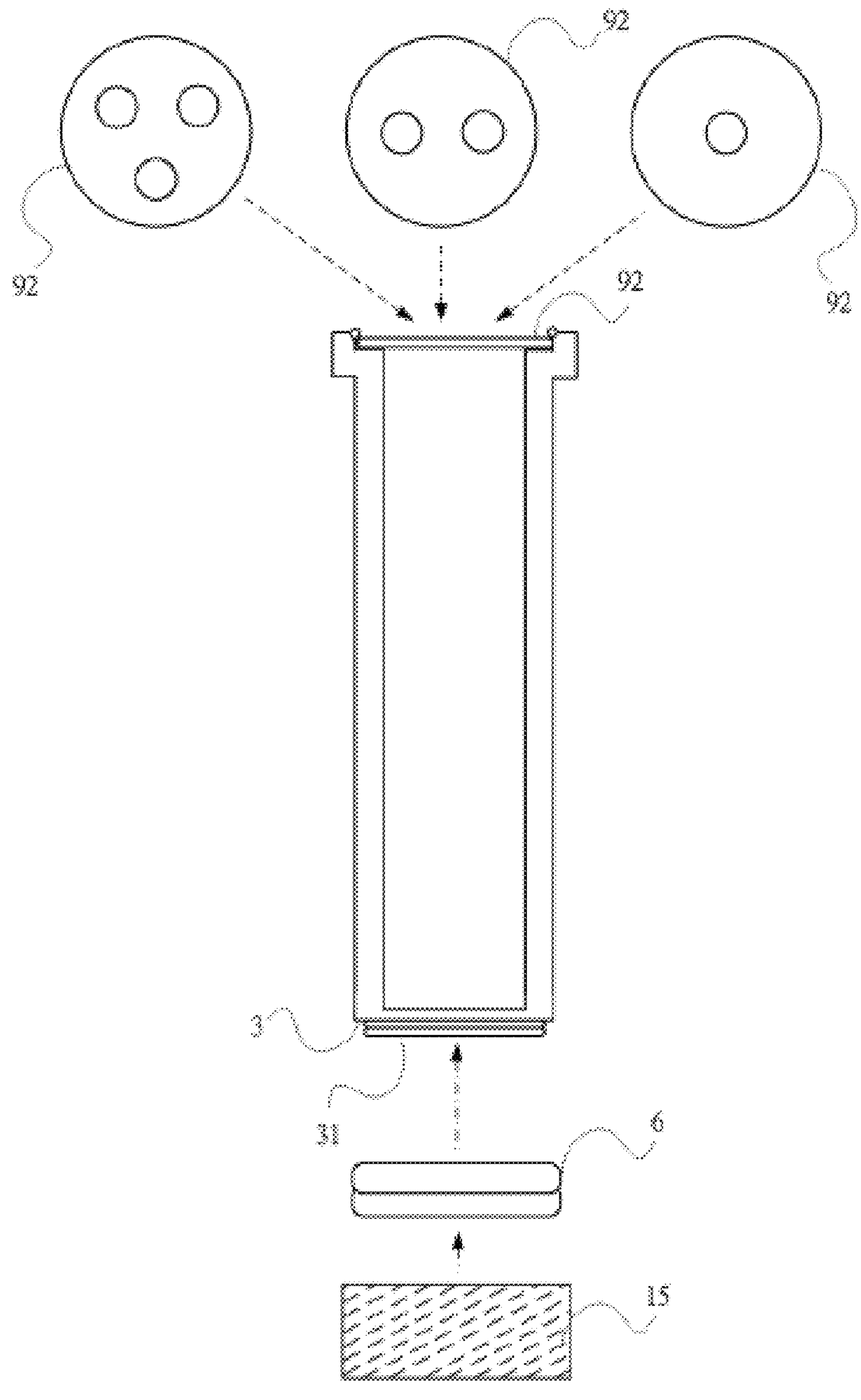
FIG. 11 Structural representation of plunger top coupling section and cushion sheet.

An embodiment of the present invention, as shown in [FIG. 11], the plunger top 3 is connected to a coupling section 31, multiple types of the push block structure 6 can be mounted to lock the movable barrier 15 to assist in pushing medicament, the push block structure 6 includes movable barrier locking, plunger top locking and movable barrier plunger top locking.

An embodiment of the present invention, as shown in [FIG. 11], a cushion sheet 92 is installed on one end of the hollow tubes, one or more than one hole can penetrate the cushion sheet 92, the sequence and rate of stretch of each section of the hollow tube can be changed by installing the cushion sheet 92 with different quantities of holes on each section of the hollow tube; the hole can be micro/nano sized to micronsized hole, so as to control the velocity of different gases.

Figure 12:
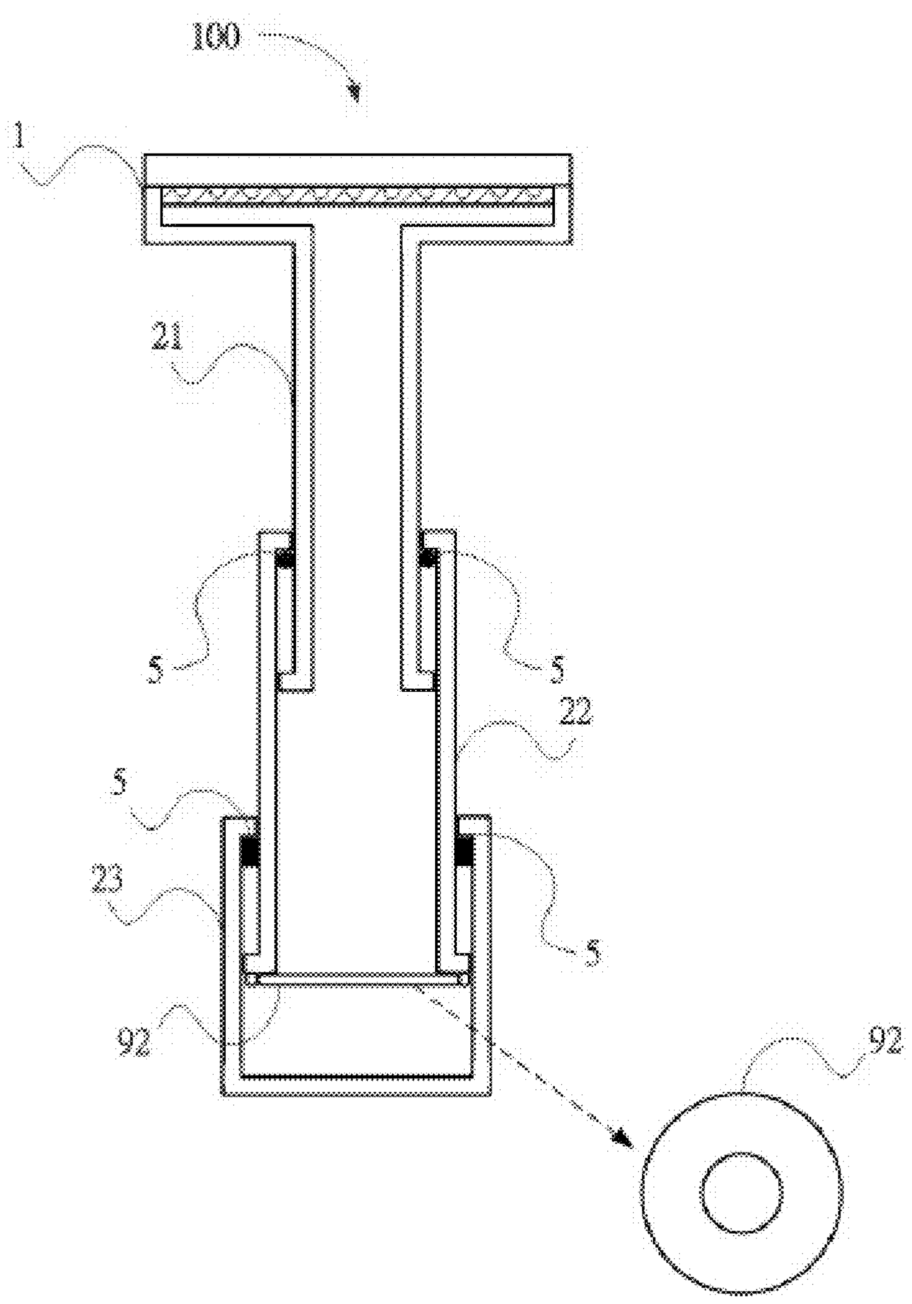
FIG. 12 Schematic diagram of variable plunger unit.

An embodiment of the present invention is shown in [FIG. 12], the cushion sheet 92 is provided with different forms of the airtight piece 9 and the hollow tube 20 in different lengths to implement variable drug supply curve, in an embodiment of the present invention, the structure of the plunger unit 2 is that the length of the second hollow tube 22 is larger than the length of the third hollow tube 23, the airtight piece 9 for the first hollow tube 21 and the second hollow tube 22 is circular, the airtight piece 9 for the second hollow tube 22 and the third hollow tube 23 is rectangular, one end of the second hollow tube 22 is equipped with the cushion sheet 92; under the effect of the cushion sheet 92, the gas generated by the gas supply unit 1 fills up the second hollow tube 22 of the gas chamber 4 at first, as the contact area of the circular airtight piece 9 and the first hollow tube 21 is smaller than the contact area of the rectangular airtight piece 9 and the third hollow tube 23, the second hollow tube 22 is stretched to the length of the first hollow tube 21 at first; and then the gas fills up the third hollow tube 23 of the gas chamber 4, the rate of stretch is lower than the rate of stretch of the second hollow tube 22 as the airtight piece 9 is rectangular; the present invention pushes relatively large volume of the medicament 13 at a relatively fast speed, and then pushes relatively small volume of the medicament 13 at a relatively slow speed.

As stated above, different drug supply speed curves can be implemented by changing the length, caliber and roughness of the hollow tube, using the shape of the airtight piece 9 and different combinations of the cushion sheet 92.

An embodiment of the present invention is shown in [FIG. 13], the multistage gas-actuated drug supply device 100 can be combined with a drug injection container 10 containing a movable barrier to form a drug supply actuating device injection needle 200, and the gas supply unit 1 is the electrochemical pump, this device can be installed on auto-injection equipment.

In the said embodiment, the electrochemical pump produces the gas slowly, the medicament in the injection needle 200 is pushed smoothly, so that the patient receiving long and continuously small volume subcutaneous injection will not be discomforted by the injection process; for the present long and continuously small volume subcutaneous injection, the shot volume and injection time are controlled by the nurse, this problem can be solved by the present invention.

Figure 14:
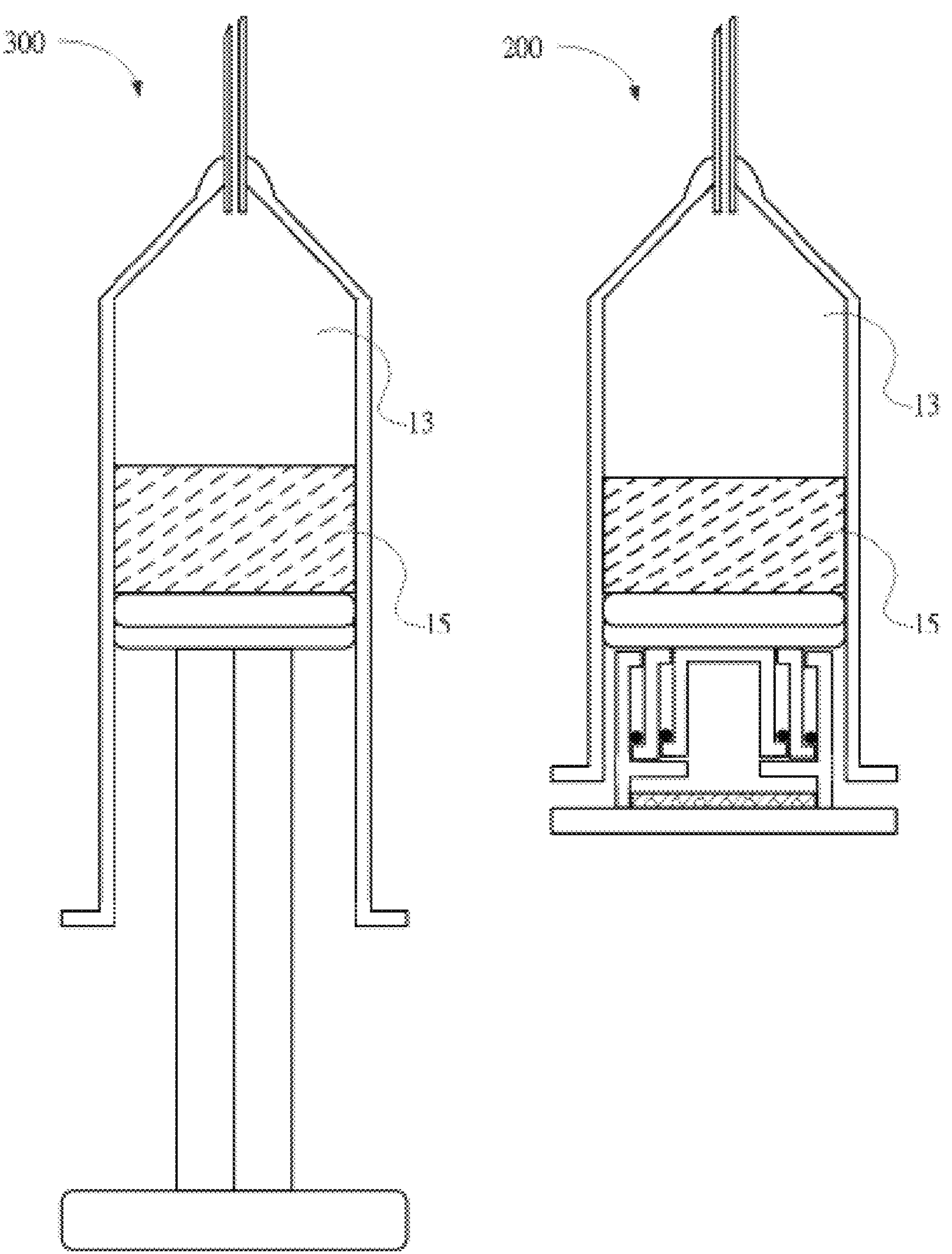
FIG. 14 Schematic diagram of injection needle of drug supply actuating device and general injection needle.

An embodiment of the present invention is shown in [FIG. 14], the drug supply actuating device injection needle 200 formed of a multistage gas-actuated drug supply device 100 of the present invention and the drug injection container 10 is compared with general injection needle 300, the present invention can effectively shorten the injection needle length.

Although the present invention has been explained in relation to its preferred embodiment, it is to be understood that many other possible modifications and variations can be made without departing from the spirit and scope of the present invention as hereinafter claimed.

The invention claimed is:

1. A multistage gas-actuated drug supply device, connected to a drug injection container, comprising:

a gas supply unit, the gas supply unit includes an electrochemical pump operable to generate a gas;

a plunger unit connected to the gas supply unit, comprising:

a plurality of hollow tubes telescopically and slidably connected to one another, an outermost hollow tube forming a plunger top, the plunger top being configured to displace a movable barrier for dispensing a medicament from the drug injection container, wherein the plurality of hollow tubes include a first hollow tube disposed innermost and a second hollow tube connected thereto, the plunger unit being connected to the gas supply unit via the first hollow tube; and a gas chamber defined by the plurality of hollow tubes and configured to receive the gas generated by the electrochemical pump;

wherein, as the gas pressure increases, the plurality of hollow tubes are actuated by the gas to move the plunger top, thereby displacing the movable barrier and dispensing the medicament, and wherein the outermost hollow tube has a uniform, continuous outer diameter throughout its entire longitudinal length.

2. The multistage gas-actuated drug supply device defined in claim 1, wherein the gas supply unit is first connected to a buffer gas chamber before being connected to the plunger unit, the buffer gas chamber functions to prevent the gas generated by the gas supply unit from directly impacting the plunger unit.

3. The multistage gas-actuated drug supply device defined in claim 1, wherein the roughness of a surface inside the hollow tubes of the plunger unit is inversely proportional to the rate of stretch of the hollow tubes, the higher the roughness is, the lower is the rate of stretch.

4. The multistage gas-actuated drug supply device defined in claim 1, wherein the hollow tubes have an airtight piece and a limit part at a coupling end of the connected hollow tubes, the limit part is designed in a concave form, a side edge height of the concave form is lower than the height of the airtight piece, so as to guarantee airtightness.

5. The multistage gas-actuated drug supply device defined in claim 1, wherein the hollow tubes have a plurality of helices, so that the hollow tubes of the plunger unit can stretch in a direction of spiral.

6. The multistage gas-actuated drug supply device defined in claim 1, wherein the plunger top is secured to the movable barrier by a coupling section.

7. The multistage gas-actuated drug supply device defined in claim 1, wherein connection between adjacent hollow tubes of the plurality of hollow tubes further comprises an annular recess defined by an outer circumferential surface of an inner hollow tube of the plurality of hollow tubes and an inner circumferential surface of an outer hollow tube of the plurality of hollow tubes, the airtight piece is disposed within the annular recess and sealing a gap between the adjacent hollow tubes of the plurality of hollow tubes to seal the gas chamber defined by the plurality of hollow tubes, and each inner hollow tube of the plurality of hollow tubes includes a limit part configured to abut an inner rim of an adjacent outer hollow tube of the plurality of hollow tubes with the airtight piece constrained therebetween upon maximum collapse.

* * * * *